United States Patent
Fischer et al.

[19]

[11] Patent Number: 5,913,863

[45] Date of Patent: Jun. 22, 1999

[54] COMPRESSION PART, AND MEDICAL COMPRESSION APPARATUS EMPLOYING SAME

[75] Inventors: Hubertus Fischer, Bamberg; Heinrich Kolem, Effeltrich; Manfred Bauer, Munich; Reiner Habrich, Kirchheim; Sylvia Heywang-Koebrunner, Engelsdorf, all of Germany

[73] Assignee: Siemens Aktiengesellschaft, Munich, Germany

[21] Appl. No.: 09/036,446

[22] Filed: Mar. 6, 1998

[30] Foreign Application Priority Data

Mar. 6, 1997 [DE] Germany .......................... 197 09 224

[51] Int. Cl.⁶ .................................................. A61B 5/055
[52] U.S. Cl. ........................................ 606/130; 600/417
[58] Field of Search ..................... 600/417, 130, 600/129, 410; 604/116

[56] References Cited

U.S. PATENT DOCUMENTS

| | | |
|---|---|---|
| 4,228,796 | 10/1980 | Gardiner .............................. 604/116 |
| 4,798,212 | 1/1989 | Arana ................................. 604/116 |
| 5,098,383 | 3/1992 | Hemmy et al. ..................... 604/116 |
| 5,437,280 | 8/1995 | Hussman .............................. 600/417 |
| 5,534,778 | 7/1996 | Loos et al. ........................... 606/130 |
| 5,569,266 | 10/1996 | Siczek .................................. 606/130 |
| 5,678,549 | 10/1997 | Heywang-Koebrunner et al. .. 600/417 |
| 5,681,327 | 10/1997 | Heywang-Koebrunner ........... 606/130 |
| 5,702,405 | 12/1997 | Heywang-Koebrunner ........... 600/130 |
| 5,711,299 | 1/1998 | Manwaring et al. ................... 600/417 |
| 5,800,353 | 9/1998 | McLaurin, Jr. ....................... 600/417 |

*Primary Examiner*—Paul J. Hirsch
*Attorney, Agent, or Firm*—Hill & Simpson

[57] ABSTRACT

In a medical compression apparatus and a compression part therefor, the compression part has a number of access openings therein allowing an instrument, such as a biopsy needle, to be inserted through one of the openings into a body part compressed by the apparatus. The compression part allows the access openings to be alterable in size and/or shape.

17 Claims, 2 Drawing Sheets

COMPRESSION PART, AND MEDICAL COMPRESSION APPARATUS EMPLOYING SAME

BACKGROUND OF THE INVENTION

1. Field of the Invention

The present invention relates to a compression part for a medical compression apparatus with access openings to a compressed or fixed body part. The invention also relates to a medical compression apparatus for the compression or fixing of a body part.

2. Description of the Prior Art

A medical compression and biopsy apparatus of the general type described above, having a compression part of the type described above, is known from German PS 44 42 609 corresponding to U.S. Pat. No. 5,702,405. The compression and biopsy apparatus specified therein is fashioned as a stereotactic auxiliary means for conducting—guided by a sectional image—a biopsy of a female breast. This known apparatus has two compression parts, arranged movably in relation to one another, for fixing the breast therebetween. The compression parts are fashioned as compression plates in which through-holes are arranged that enable a guided access of a biopsy needle to the breast. The precision of the biopsy, however, is limited by the fixed, grid-like arrangement of the through-holes in the compression plate.

A further compression apparatus is known from German PS 42 25 001, corresponding to U.S. Pat. No. 5,678,549, in which the compression plates are movably arranged on a mount in the form of a bar, and can be secured at respective locations along the length of the bar since the bar is made of round material, by pivoting the compression plates the aforementioned precision problem could be solved. Pivoting of the plates is possible only in the non-compressed state. The danger of a change in position of the target area thus exists.

In addition, since the through-holes have only a small diameter due to their guide characteristics, cleaning and sterilization of the compression plates for repeated uses is expensive.

SUMMARY OF THE INVENTION

An object of the present invention is to provide a compression part with which a body part to be examined can be sufficiently fixed, and in which a puncture location and puncture direction of a biopsy needle can be freely selected. In addition, in for enabling repeated use the compression part should be easy to clean and to sterilize. In addition, it is an object of the present invention to provide a medical compression and biopsy apparatus in which the puncture location and puncture direction of a biopsy needle can be freely selected.

The first object is achieved in accordance with the invention in a compression part having access openings that are fashioned so as to be individually alterable. If the compression part material limiting the access openings is covering an optimal puncture location, then even in the compressed state the access opening can be altered in such a way that its edge no longer covers the optimal puncture location. The size and/or shape of the access openings is advantageously fashioned so as to be alterable. The size of the access opening is selected in such a way that a sufficient compression or fixing of the body part becomes possible.

In an embodiment, each access opening is limited at least partially by webs that are fashioned so as to be rigid in one compression/decompression direction and to be elastic in a direction transversely thereto. The webs are provided for the compression or fixing of the body part, and due to their elasticity can be altered easily in their position so that they do not hinder the biopsy. The displacement of one or several disturbing webs can ensue in the compression or fixing position of the compression part, e.g. using a spreading apparatus.

In a version of this embodiment the webs in the longitudinal direction are respectively fastened at the end side to a rigid frame part. The compression part is thus easy to handle, and can be inserted into a changing frame.

In a further version the webs in the compression/decompression direction are fashioned to be broader at one side than the frame parts. An asymmetrical construction of the compression part thereby results with respect to the lateral frame parts. Depending on which side of the compression part is facing the body part to be examined, body parts varying greatly in size can be compressed and fixed for examination, even given only limited positioning possibilities of the movable frame into which the compression part can be inserted.

In a further version the webs and the frame parts are of one-piece construction. This yields advantages in the manufacturing of the compression part, since it can be cast in one piece, e.g. in a mold. Advantages in use also arise in cleaning and sterilization, since no joints, cracks or the like are present in the compression part.

The second object is achieved in a medical compression apparatus having an inventive compression part as described above which is inserted into at least one holding frame that can be moved in a compression/decompression direction.

A precise guiding of a biopsy needle is achieved according to a further embodiment a biopsy needle guide is arranged separately from the compression part.

DESCRIPTION OF THE PREFERRED EMBODIMENTS

Figure 1:
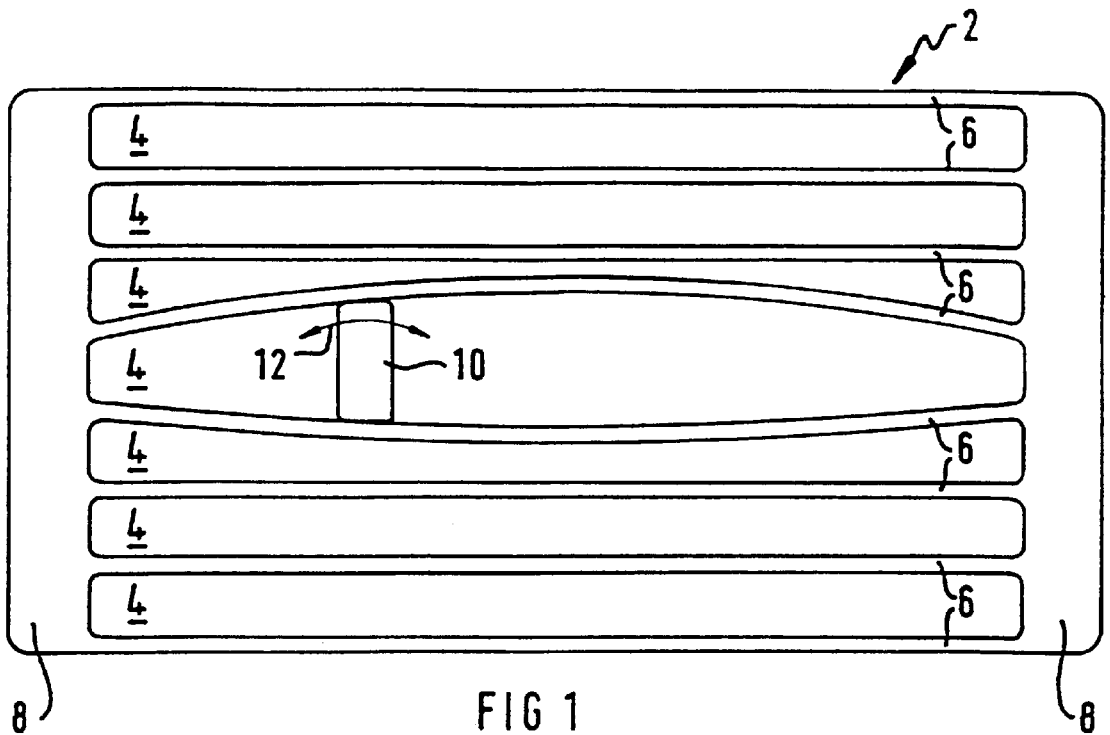
FIG. 1 shows, in a top view, a compression part with a spreader element, constructed in accordance with the principles of the present invention.

The compression part 2 shown in a top view in FIG. 1 is provided for use in a medical compression and biopsy apparatus, fashioned for conducting—guided by a sectional image—a biopsy of a female breast. The surface, visible in the top view of FIG. 1, of the compression part 2 transmits compression forces, necessary for fixing, to the body part to be examined. The compression part 2 has seven rectangularly formed access openings 4 that enable access of a biopsy needle to the body part to be examined. The size of the access openings 4 is basically determined by the deformability and resilience of the body part to be examined. Body parts having less resilient tissue permit larger access openings than do body parts having softer tissue parts. For breast examinations, the access openings are constructed e.g. with dimensions of about 2 cm×26 cm. The size of the access openings 4 can be altered, in order to avoid hindrances that would otherwise be present to the accessibility to the body part to be examined. For this purpose, the access openings 4 on the opposed longitudinal sides are limited by webs 6 that are fashioned so as to be rigid in one compression/decompression direction and to be elastic transverse to this direction. In the longitudinal direction, the webs 6 are respectively fastened at their ends to a rigid frame part 8.

Using a cuboid spreader piece 10, an access opening 4 can be enlarged in order to release an optimal puncture point for the biopsy needle. The spreader piece 10 can in principle be set flat on an arbitrary point in the access opening 4, in order to spread the adjacent webs away from one another after rotation (curved double arrow 12). The spreader piece 10 is held in the spreading position by the pressure forces exerted by the webs 6. After removal of the spreader piece 10, the previously spread webs 6 return to their initial position.

Figure 2:
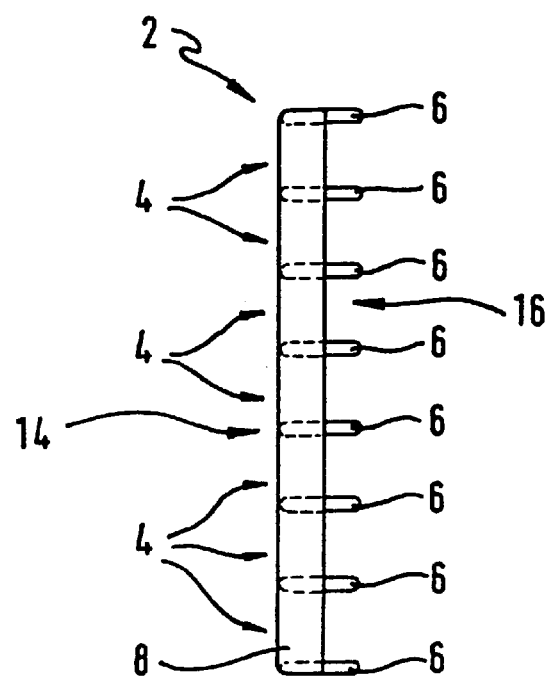
FIG. 2 shows a side view of the compression part according to FIG. 1, but without the spreader element.

FIG. 2 shows, in a side view, the compression part 2, but without the spreader piece 10. The webs 6 are fashioned so as to be broader on one side in the direction of compression/decompression than the frame parts 8; they thus protrude on one side in the compression/decompression direction with respect to the frame parts 8. Depending on how the compression part 2 is set into the compression and biopsy apparatus, larger or smaller body parts can be compressed and fixed. For this purpose, both the left side 14 and also the right side 16 are fashioned for compression and fixing of the body part.

The compression part 2 has neither sharp edges nor, for facilitating cleaning, inaccessible corners. The transitions from the webs 6 to the frame parts 8 are as rounded, as are the edges of the webs 6 and of the frame parts 8. The webs 6 thus have an almost oval cross-section.

The compression part 2 is manufactured from epoxy resin by casting it from one piece in a mold.

Figure 3:
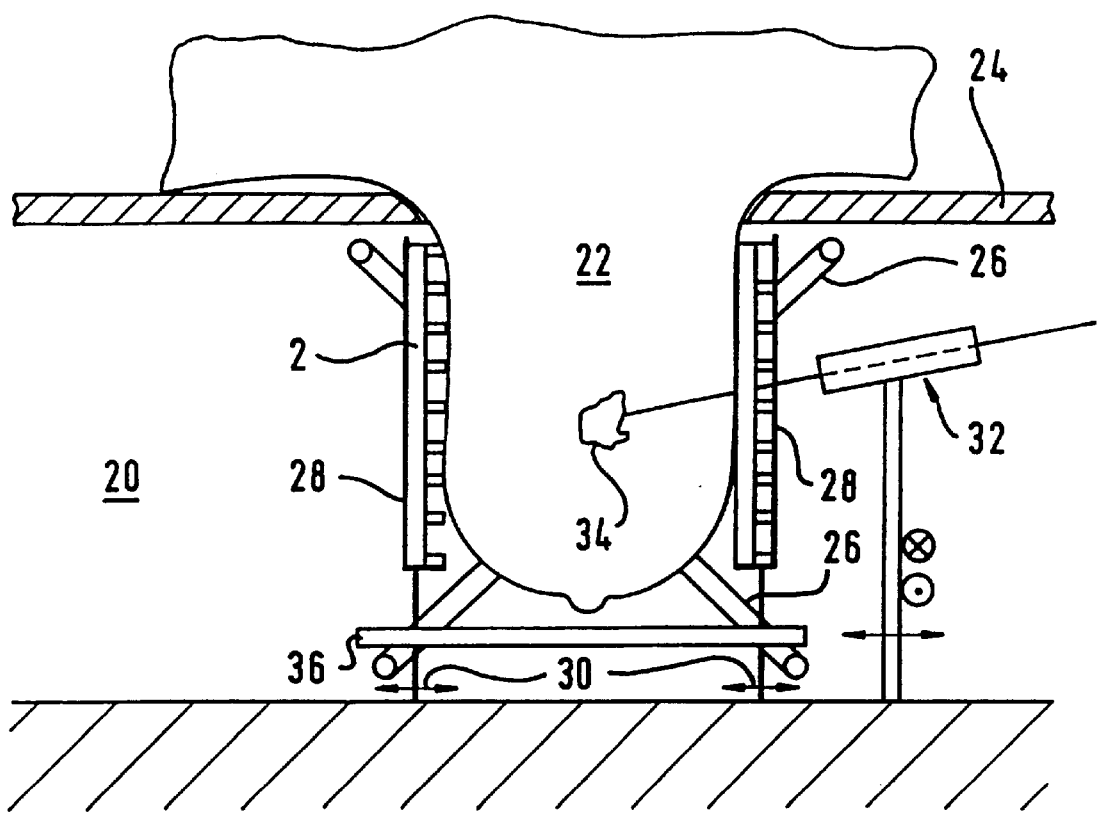
FIG. 3 shows, in a side view, the basic construction of a compression and biopsy apparatus with two inventive compression parts.

FIG. 3 shows a sectional representation, in a side view, of the basic construction of a compression and biopsy apparatus 20 for carrying out a biopsy on a female breast 22, under monitoring by magnetic resonance tomograms. The examination is carried out with the patient lying in a prone position, the breast 22 being placed into the examination chamber of the compression and biopsy apparatus 20 via an opening in a patient table 24.

The compression and biopsy apparatus 20 is located inside an antenna arrangement 26 that is constructed for the reception of magnetic resonance signals from the examination chamber. The antenna arrangement 26 belongs to a conventional magnetic resonance tomography apparatus, described in many other documents.

For the compression and fixing of the breast 22 in an examination position, the compression and biopsy apparatus 20 has holding frames 28 arranged movably in relation to one another that can be secured in the examination position. The displacability of the holding frames 28 is respectively symbolized by a double arrow 30. The holding frames 28 are constructed in a U-shape, so that the compression parts 2 can be inserted and removed from above. For the compression part 2 shown at the left in the compression and biopsy apparatus 20, the compressing surface is that side in which the webs are broader than the holding parts 8. For the compression part 2 shown at the right, the compressing surface is the side in which the webs 6 terminate flush with the frame parts.

A biopsy needle guide 32 is arranged separately from the compression parts 2, fastened in height-adjustable fashion on a movable stand that can be fixed in an arbitrary position. The orientation of the needle guide 32 is likewise arbitrarily adjustable, so that each region 34 to be punctured can be reached via an appropriate path. A suitable needle guide can be obtained, for example, from the company Fisher Imaging Corp., Denver, Colo., USA.

In order to enable an allocation of the findings in the magnetic resonance tomogram to the actual anatomical position, a marking apparatus 36, in the form of a tube filled with a contrast agent, is allocated to the compression and biopsy apparatus 20. The tube is arranged underneath the holding frame 28 in the detection area of the antenna arrangement 26, and is oriented along the of compression/decompression direction.

Although modifications and changes may be suggested by those skilled in the art, it is the intention of the inventors to embody within the patent warranted hereon all changes and modifications as reasonably and properly come within the scope of their contribution to the art.

We claim as our invention:

1. A compression part for use in a medical compression apparatus, a compression part comprising a plurality of access openings allowing access through said compression part to a compressed body adjacent said compression part, said access openings being individually alterable.

2. A compression part as claimed in claim 1 wherein said access openings are alterable in size.

3. A compression part as claimed in claim 1 wherein said access openings are alterable in shape.

4. A compression part as claimed in claim 1 wherein said access openings are alterable in size and shape.

5. A compression part as claimed in claim 1 comprising a plurality of webs, each web at least partially limiting one access opening, and said webs being rigid in a compression/decompression direction and elastic in a direction transverse to said compression/decompression direction.

6. A compression part as claimed in claim 5 wherein each of said webs has a longitudinal axis, with the longitudinal axis of each web being transverse to said compression/decompression direction.

7. A compression part as claimed in claim 6 wherein said webs are spaced from each other in a further direction transverse to said compression/decompression direction and transverse to each longitudinal axis.

8. A compression part as claimed in claim 7 wherein said webs are parallel to each other and equally spaced from each other.

9. A compression part as claimed in claim 5 further comprising a rigid frame part surrounding said webs, with each web having opposite ends attached to a side of said rigid frame part.

10. A compression part as claimed in claim 9 wherein said frame part has a longitudinal direction transverse to a longitudinal direction of said webs.

11. A compression part as claimed in claim 9 wherein each web has a side at which each web is broader than said frame part in said compression/decompression direction.

12. A compression part as claimed in claim 9 wherein said webs and said frame part comprise a unitary piece.

13. A medical compression apparatus comprising:

first and second compression plates;

means for mounting said compression plates relative to each other for allowing movement of at least one compression plate relative to the other in a compression/decompression direction for compressing a body part between said compression plates;

at least one of said compression plates comprising a holding frame and a compression part removably insertable into said holding frame; and said compression part comprising a plurality of access openings which are individually alterable.

14. A medical compression apparatus as claimed in claim 13 wherein said compression part comprises access openings which are alterable in size.

15. A medical compression apparatus as claimed in claim 13 wherein said compression part comprises access openings which are alterable in shape.

16. A medical compression apparatus as claimed in claim 13 wherein said compression part comprises access openings which are alterable in size and in shape.

17. A medical compression apparatus as claimed in claim 13 further comprising a biopsy needle guide disposed separately from said compression part.

* * * * *